Figure 1A:
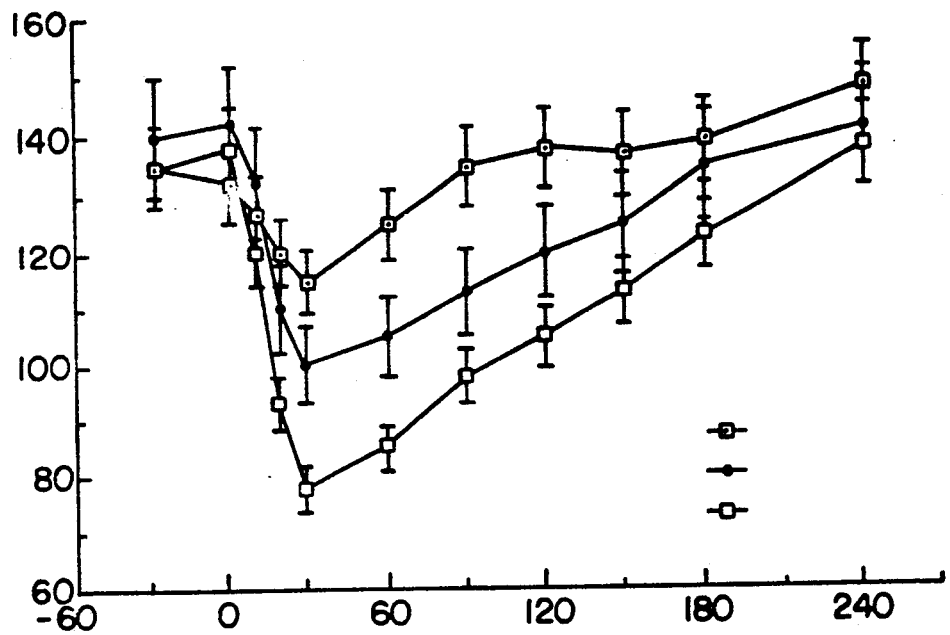

United States Patent [19]

Melchiorri et al.

[11] Patent Number: 5,013,721
[45] Date of Patent: May 7, 1991

[54] ANOREXIGENIC AND HYPOTENSIVE PEPTIDES

[75] Inventors: Pietro Melchiorri; Lucia Negri, both of Segrate, Italy

[73] Assignee: Zambon Group S.P.A., Vincenza, Italy

[21] Appl. No.: 368,662

[22] Filed: Jun. 20, 1989

[30] Foreign Application Priority Data

Jul. 1, 1988 [IT] Italy .................... 21191 A/88

[51] Int. Cl.$^5$ .................. C07K 7/10; A61K 37/02
[52] U.S. Cl. ..................................... 514/13; 514/14; 514/15; 530/327; 530/326
[58] Field of Search ............ 530/327, 326; 514/13, 514/14, 15

[56] References Cited

U.S. PATENT DOCUMENTS 4,613,586  9/1986  Barchas et al. ............... 514/15

OTHER PUBLICATIONS

Stewart et al., *Solid Phase Peptide Synthesis*, Pierce Chemical Co., pp. XV, 1984.
Stedman, *Stedman's Medical Dictionary*, 24th ed., Williams & Wilkins, pp. 1178, 1982.
Itoh et al., *Peptides*, 6:53–57, 1985.
Melchiorri, P. et al., *Regulatory Peptides*, 2:1–13, 1981.
Erspamer, V. et al., Naunyn-Schiedeberg's Arch. Pharmacol. 312:265–270 (1980).
Falconieri, G. et al., *Regulatory Peptides*, 21:1–11, 1988.
Erspamer, V. et al., *Peptides*, vol. 2, (Suppl. 2): 7–16, 1981.
Barra, D. et al., *Febs Letters*, 182(1):53–56, Mar. 1985.
Gozzin, L. et al., Int. J. Peptide Protein Res., 25:323–329, 1985.
Erspamer, V. et al., *Neuropharmacology*, 24(8):783–792, 1985.
Negri, L. et al., Ann. N.Y. Acad. Sci., 547:415–428, 1988.
Negri. L. Eur. J. of Pharmacol., 132:207–212, 1986.

*Primary Examiner*—Jeffrey E. Russel
*Assistant Examiner*—Susan M. Perkins
*Attorney, Agent, or Firm*—Walter H. Schneider

[57] ABSTRACT

Novel peptides having anorexigenic and hypotensive activities, of general formula:

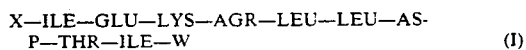

wherein X is an amino acid residue or a peptide chain selected from the group consisting of:

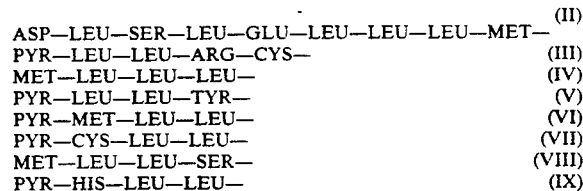

and W is a hydroxy or amino group.

5 Claims, 2 Drawing Sheets

ANOREXIGENIC AND HYPOTENSIVE PEPTIDES

The present invention relates to novel biologically active peptides, having anorexigenic and hypotensive activities, to the chemical preparation thereof and to the use thereof for the formulation of pharmaceutical preparations for therapeutical administration.

The peptides of the invention have the following general formula:

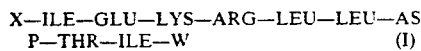

X—ILE—GLU—LYS—ARG—LEU—LEU—ASP—THR—ILE—W  (I)

wherein X is an amino acid residue or a peptide chain selected from the group consisting of:

| | |
|---|---|
| ASP—LEU—SER—LEU— | (II) |
| GLU—LEU—LEU—LEU—MET— | |
| GLU—LEU—LEU—ARG—CYS— | (III) |
| MET—LEU—LEU—LEU— | (IV) |
| GLU—LEU—LEU—TYR— | (V) |
| GLU—MET—LEU—LEU— | (VI) |
| GLU—CYS—LEU—LEU— | (VII) |
| MET—LEU—LEU—SER— | (VIII) |
| GLU—HIS—LEU—LEU— | (IX) | and W is a hydroxy or amino group.

Particularly preferred peptides are those in which X is one of the peptide residues (II), (III), (IV) and (V) cited above.

The peptides of the invention have the following pharmacological characteristics:
- anorexigenic activity in mouse, rat, dog, monkey and man, by administration of an effective amount of the peptides by transcutaneous, transmucosal and inhalatory routes, in form of pharmaceutical compositions such as ointments, creams, slow release patches, microtablets for the sublingual use, nasal sprays, chewing gums, sugar-drops and injectable solutions;
- hypotensive action in the same animal species administered in the same form of pharmaceutical compositions.

The anorexigenic action lasts, on the average, 4 to 6 hours, the hypotensive one about 3 to 5 hours. Both actions are of the peripheral type, as the above cited peptides do not significantly cross the hematoencephalic barrier. Therefore, the therapeutical uses in human patients are evident and they can be related to the treatment of hypertensive syndromes and of different hyperphagia and obesity conditions.

The peptides of the present invention can be prepared in solid phase on polymeric supports. The preparation starts from the C-terminal amino acid which is grafted in a first step to a methylbenzhydrylamine, benzhydrylamine or chloromethylated resin. The other amino acids are grafted step by step, after having protected the side chains thereof. Protective groups for the side chains of the Ser, Thr, Asp, Glu and His residues are well known in the art. After that, the whole protected peptide is released either from the chloromethylated resin by ammoniolysis to obtain the protected amide, or from the methylbenzhydrylamine or benzhydrylamine resins by treatment with hydrofluoric acid at 0° C., to obtain at the same time the release from the resin and deprotection.

The t-butoxycarbonyl (BOC) group is preferably used to protect the α-amino group. The basis for selecting the protective groups for the side chains is that said groups must not be removed when BOC is removed from the α-amino group, step by step, during the preparation.

The following examples and tests illustrate the preparation of some peptides of the invention and the pharmacological properties thereof.

EXAMPLE 1

Preparation of the amino acid sequence common to all the peptides of the invention, having formula ILE—GLU—LYS—ARG—LEU—LEU—ASP—THR—ILE—$NH_2$ A benzhydrylamine resin (6 g) is used for the preparation in solid phase, to which resin the BOC-ILE amino acid (C-terminal) is grafted, dissolved in 50 ml of 10% dimethylformamide in dichloromethane, using a 3 times excess in the BOC-derivative and dicyclohexylamide as the activating agent, during 2 hours. The isoleucine residue is thus grafted to the resin by an amido bond. THR alcoholic group is previously protected by means of the tert-butyl group, before grafting the amino acid to the peptide chain. Each amino acid is added to the peptide chain by the following program, using the Beckman 990B synthetizer in solid phase:

1. washing with 2×80 ml portions of dichloromethane, 3 minutes;
2. washing with 2×39 ml portions of methanol, 3 minutes;
3. washing with 3×80 ml portions of dichloromethane, 3 minutes;
4. 2×50% TEA plus 5% 1,2-ethanethiol in dichloromethane (70 ml), 10 minutes;
5. washing with 2×80 ml portions of dichloromethane, 3 minutes;
6. 2×12,5% TEA in 70 ml dichloromethane, 5 minutes;
7. washing with 2×40 ml portions of methanol, 2 minutes;
8. washing with 3×80 ml portions of dichloromethane, 3 minutes;
9. BOC-amino acid (10 mmoles) in 30 ml of dichloromethane or dimethylformamide plus dicyclohexylcarbodiimide (10 mmoles) in dichloromethane (50–300 minutes);
10. washing with 3×40 ml portions of methanol, 3 minutes;
11. 12,5% TEA in dichloromethane (70 ml), 3 minutes;
12. washing with 2×30 ml portions of methanol, 3 minutes;
13. washing with 2×80 ml portions of dichloromethane, 3 minutes.

At step 13 a sample is withdrawn which must be negative under the ninhidrine test if the amino acid is grafted; in that instance the sequence is carried out again to graft the subsequent amino acid. If the test is positive, the cycle is repeated from 9 to 13.

When the sequence is completed, the peptide is released from the resin and the side chains are deprotected by treatment at −20° C. for 30 minutes, and subsequently at 0° C. for 40 minutes, with 15 ml of HF per gram of resin-peptide compound, previous addition of anisol (2,0 ml) and methyl ethyl sulfide (0,5 ml) per gram.

Hydrofluoric acid is removed under vacuum and the resin is washed with ether and extracted with 50% acetic acid. The extract containing the crude peptide is lyophilized. Purification is carried out first on a Sephadex G 25 column, using a n-butanol, acetic acid and water 5:1:4 by volume mixture as the eluent, then by semipreparative HPLC on a 25 cm×10 mm Supelcosil SPLC 18-08 column, using as the eluent an acetonitrile gradient varying from 18 to 45% in a 0,1% trifluoroacetic acid aqueous solution.

After purification by HPCL, the obtained purity is 98%. The thus purified nonapeptide shows a single peak by HPLC, with a retention time in the above described system of 12,7 minutes and an optical power of $[\alpha]_D^{23} = -52 \pm 1$.

EXAMPLES 2 to 5

According to a procedure similar to the one described in Example 1, the following peptides were obtained:

Peptide II: ASP—LEU—SER—LEU—GLU—LEU—LEU—MET—ILE—GLU—LYS—ARG—LEU—LEU—ASP—THR—ILE—NH$_2$;
opticale power $[\alpha]_D^{23} = -44 \pm 1$;

Peptide III: PGLU—LEU—LEU—ARG—CYS—ILE—GLU—LYS—ARG—LEU—LEU25—ASP—THR—ILE—NH$_2$;
optical power $[\alpha]_D^{23} = -32 \pm 1$;

Peptide IV: MET—LEU—LEU—LEU—ILE—GLU—LYS—ARG—LEU—LEU—ASP—THR—ILE—NH$_2$;
optical power $[\alpha]_D^{23} = -27 \pm 1$;

Pharmacological properties

The peptides of the invention are anorexigenic and hypotensive in all the tested animals, including man, both by acute administration and by administration prolonged for more than 3 months. By way of example, the tests relating to Peptide II, carried out respectively in the rat and in the monkey (Macaca mulatta), are reported hereinbelow.

Anorexigenic and hypotensive activities in the rat

Peptide II dissolved in physiological saline was injected subcutaneously in 20 male Wistar rats, of average weight 200 g, fasted for 48 hours. Twenty other rats (controls) of the same strain, sex and weight, fasted for the same time, were injected subcutaneously with only solvent. The food amount ingested by the animals in the subsequent 12 hours after the injections was measured with a ±0,1 g precision.

The hypotensive action, measured by incruent determination of the arterial pressure by means of sphygmomanometric sleeve placed on the tail of the conscious kept at 28° C., is evidenced at 15-20 µg/kg doses and, at 200 µg/kg doses, it consists in a maximum pressure decrease of 60 mm Hg, with a duration of about 4 hours.

The peptide dose inhibiting by 50% the food ingestion, is 5 µg/kg body weight. With a 10 µg/kg dose inhibitory action on food ingestion lasts for more than 12 hours.

Figure 1B:
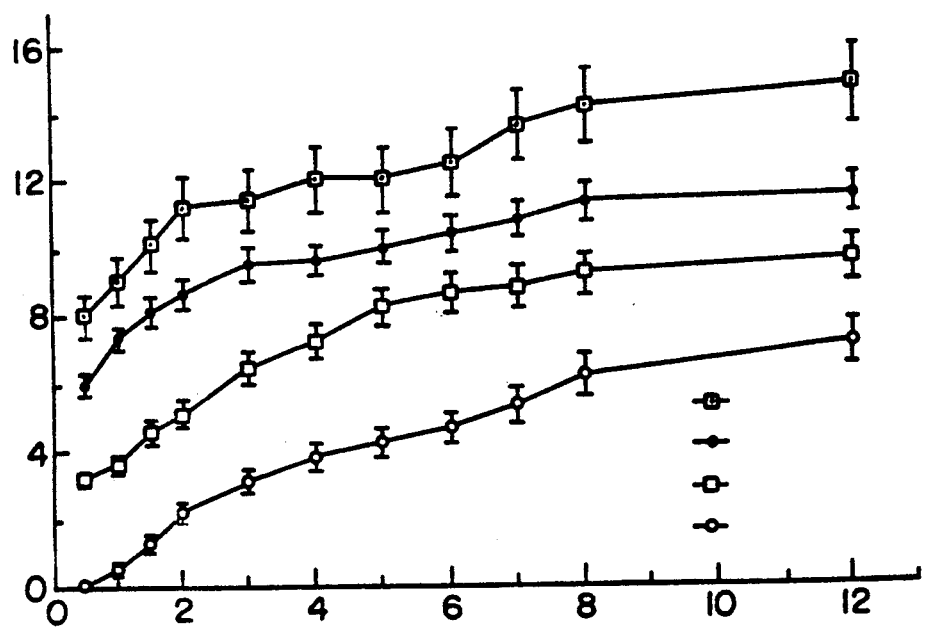

FIG. 1a illustrates the dose-effect relationship relating to the hypotensive action in the rat while FIG. 1b shows the dose-effect relationship relating to the anorexigenic action.

Anorexigenic and hypotensive activities in the monkey

Peptide II was injected subcutaneously to 3 Macaca mulatta monkeys weighing 25 kg, males, fasted for 24 hours.

The same animals were used as controls, measuring the food amount which they ingested during 8 hours, after 24 hours fasting, in the week before the peptide injection and in the subsequent one.

Figure 2A:
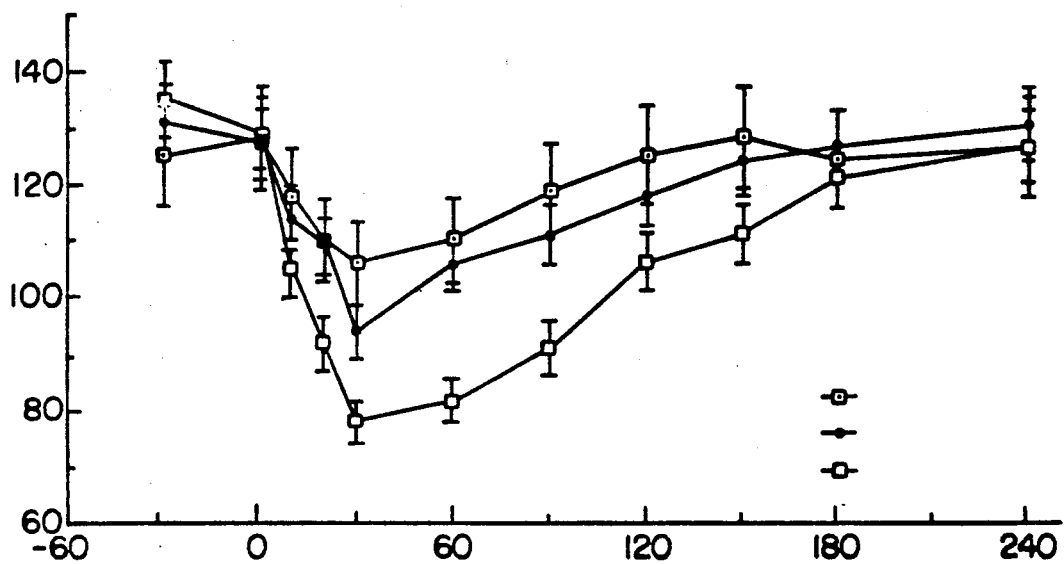
Figure 2B:
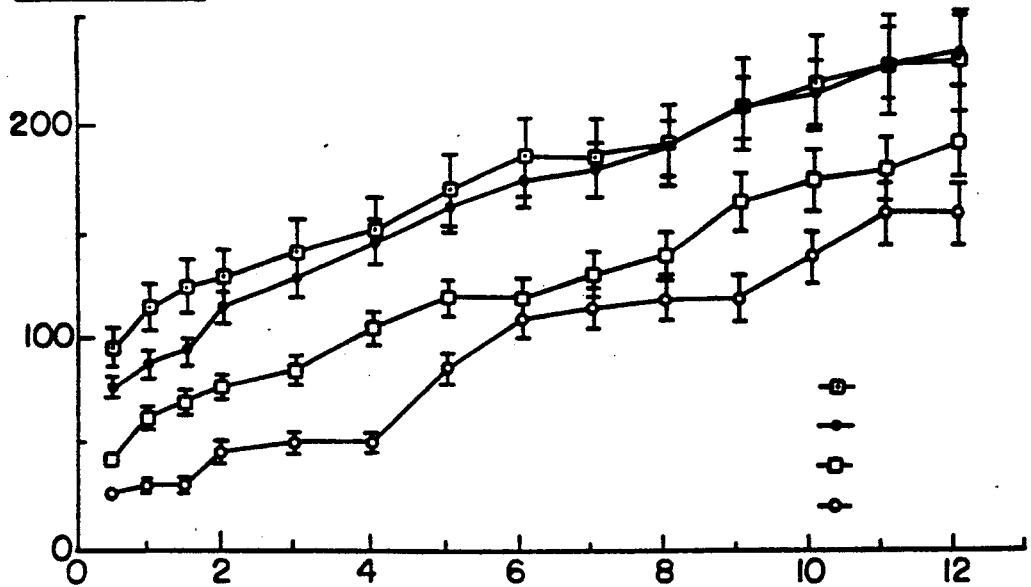

FIGS. 2a and 2b respectively show the inhibitory effect of 3 doses of the peptide (10, 20, 30 µg/kg) on food ingestion and the hypotensive effect (arterial pressure of the femoral artery) of 50, 100, 200 µg/kg of the peptide in the monkey. The dose inhibiting by 50% food ingestion is 20 µg/kg, whereas a pressure decrease of 25 mm Hg is obtained with a 200 µg/kg dose.

The hypotensive effect lasts about 4 hours, whereas the anorexigenic one reaches about 12 hours.

I claim:

1. A peptide of the general formula:

X—ILE—GLU—LYS—ARG—LEU—ASP—THR—ILE—W    (I)

wherein X is an amino acid residue or a peptide chain selected from the group consisting of:

| | |
|---|---|
| ASP—LEU—SER—LEU GLU—LEU—LEU—LEU—MET— | (II) |
| pGLU—LEU—LEU—ARG—CYS— | (III) |
| MET—LEU—LEU—LEU— | (IV) |
| pGLU—LEU—LEU—TYR— | (V) |
| pGLU—MET—LEU—LEU— | (VI) |
| pGLU—CYS—LEU—LEU— | (VII) |
| MET—LEU—LEU—SER— | (VIII) |
| pGLU—HIS—LEU—LEU— | (IX) | and W is a hydroxy or amino group.

2. A peptide according to claim 1 in which the peptide chain is selected from (II), (III), (IV), (V).

3. A pharmaceutical composition having anorexigenic and hypotensive activities comprising as the principal active ingredient an effective amount of a peptide according to claim 1 in admixture with a pharmaceutically acceptable carrier.

4. A pharmaceutical composition having anorexigenic and hypotensive activities comprising as the principal active ingredient an effective amount of a peptide according to claim 1 in admixture with a pharmaceutically acceptable carrier.

5. A pharmaceutical composition according to claim 3 in which the composition is in a form suitable for administration by any of the subcutaneous, transcutaneous, transmucosal and inhalatory routes.

* * * * *